United States Patent [19]

Ralfs et al.

[11] Patent Number: 4,840,070
[45] Date of Patent: Jun. 20, 1989

[54] LAMINATE COMPRESSION TESTER

[75] Inventors: Colin A. Ralfs; Anthony Murdock, both of Preston, United Kingdom

[73] Assignee: British Aerospace Public Limited Company, Preston, England

[21] Appl. No.: 110,310

[22] Filed: Oct. 20, 1987

[30] Foreign Application Priority Data

Oct. 21, 1986 [GB] United Kingdom ............... 8625204

[51] Int. Cl.$^4$ .............................................. G01N 3/08
[52] U.S. Cl. ...................................................... 73/818
[58] Field of Search ................ 73/860, 859, 857, 856, 73/818, 821, 819, 825, 858, 846, 841, 845, 849, 851, 853, 854

[56] References Cited

U.S. PATENT DOCUMENTS

| | | | |
|---|---|---|---|
| 3,358,498 | 12/1967 | Wright | 73/860 |
| 3,559,473 | 2/1971 | Dudderas et al. | |
| 3,757,568 | 9/1973 | Fletcher et al. | 73/856 |
| 3,795,134 | 3/1974 | Eichenbrenner et al. | |

FOREIGN PATENT DOCUMENTS

| | | | |
|---|---|---|---|
| 532783 | 10/1976 | U.S.S.R. | 73/821 |
| 0932358 | 5/1982 | U.S.S.R. | 73/818 |
| 480060 | 2/1938 | United Kingdom . | |
| 987400 | 3/1965 | United Kingdom . | |
| 2151798 | 7/1985 | United Kingdom . | |

Primary Examiner—Stewart J. Levy
Assistant Examiner—Robert R. Raevis
Attorney, Agent, or Firm—Cushman, Darby & Cushman

[57] ABSTRACT

Apparatus for limiting the buckling of an elongate test specimen during a compression test comprises a stabilizer through which the specimen 6 passes when assembled into a testing machine, the stabilizer having a body 1, 4 which is arranged to hold stiff stabilizing rods 2, 3 adjacent to those opposite faces of the specimen liable to buckle. The rods 2, 3 are adjustable to accommodate specimens 6 of different thicknesses. The stabilizer slidably engages the specimen grips 11 of the testing machine and is supported thereby so that premature shear failure of the specimen adjacent to the grips is also prevented.

6 Claims, 3 Drawing Sheets

LAMINATE COMPRESSION TESTER

BACKGROUND OF THE INVENTION

This invention relates to the compression testing of materials and in particular to the testing of laminate samples.

It is known to test materials, to establish compression and shear parameters by placing test specimens of the material into a press and compressing them until they fail. An established method of testing a laminate sample of composite materials is to bond strain gauges and clamping surfaces to its surfaces and then to clamp it in a press. The sample is then subjected to a load and compressed until it fails. Deformation of the specimen is detected by the strain gauges and recorded against load so that the behaviour of the material can be analysed under different loads. The ends of the specimen usually have a plastic material bonded to them to prevent the sample failing at the points where it is gripped by the press. Irregularities in the grips of the press often cause localised points of stress which nip the ends of the sample and cause it to fail. Plastic pads smooth out irregularities and spread the load evenly over each end of the specimen.

This method of testing samples is time consuming and costly. Because the strain gauges are bonded to the specimen under test it is not practical to remove them for re-use, consequently a new set of strain gauges is required for each sample to be tested which are then discarded with the specimen after test. Similarly applying uniform layers of plastic to the ends of each specimen is a time consuming and costly business.

Another problem arises when analysing specimens of multi angular laminates which compress to a considerable extent before they begin to fail, consequently very long samples are required for a compression test. The problem is that long strips are flexible and liable to buckle and snap before they have compressed very far. A method of overcoming failure of samples due to buckling is to place a stabiliser around the specimen to prevent it from flexing outwardly and snapping. One form of stabiliser, for example, consists of a solid rod of material with a slot along one side. The sample to be tested has its edge placed inside the slot and is then compressed; buckling of the sample is limited to the width of the slot which is just sufficient to allow failure of the sample due to compression.

A disadvantage of such stabilisers is that they are of a fixed slot width and limited to one particular specimen thickness, so different stabilisers are required for different specimens widths. Another problem encountered with fixed stabiliser arrangements is that the samples frequently jam tight into the stabiliser after failing and they are difficult to remove before inserting the next sample. The stabiliser is sometimes itself a source of failure if for instance the stabiliser should move laterally during compression of the sample it can cause the specimen to kink and sheer at the ends of the stabiliser.

A large number of specially prepared specimens are usually required to test for compression failure because many of the samples will snap due to nipping, buckling or kinking before they have reached the limit of their compressive properties and this increases the expense of the test. It would therefore be an advantage if a system could be implemented to eliminate failures due nipping, buckling or kinking so that specimens could be consistently induced to fail by compression. An object of the present invention is to eliminate such failures and reduce the time and cost of processing each specimen.

SUMMARY OF THE INVENTION

According to one aspect of this invention there is provided apparatus for limiting the buckling of a specimen during a compression failure test, said apparatus comprising a stabiliser for constraining the specimen during compression comprising co-operatng bracket members adapted for slidable mounting in a compression test machine which are adjustably secured to each other so as to accept different thickness specimens. Conveniently the ends of the stabiliser brackets are so shaped and arranged to co-operate with gripping inserts of said machine that specimen buckling limiting faces of the stabiliser brackets always remain at a pre-determined distance from the specimen.

Preferably the stabiliser brackets are arranged to engage with the gripping inserts of a compression machine and to prevent lateral movement of the stabiliser with respect to the compression machine.

According to another aspect of this invention there is provided a re-useable extensometer bridge which is attached to a specimen to measure deformation of the specimen in at least one dimension.

According to yet another aspect of this invention there is provided spark eroded grip inserts for gripping the specimen in a compression test machine.

A specific embodiment of the invention will now be described by way of example only and with reference to the accompanying drawings in which: BRIEF DESCRIPTION OF THE DRAWINGS FIG. 1 is a side view of part of a compression test apparatus, a laminate specimen under test, and a stabiliser, FIG. 2 is an enlarged detail of part of the arrangement of FIG. 1, and FIG. 3 is a perspective view of a stabiliser with a specimen mounted for test inside.

DETAILED DESCRIPTION OF THE INVENTION

Figures 1, 2:
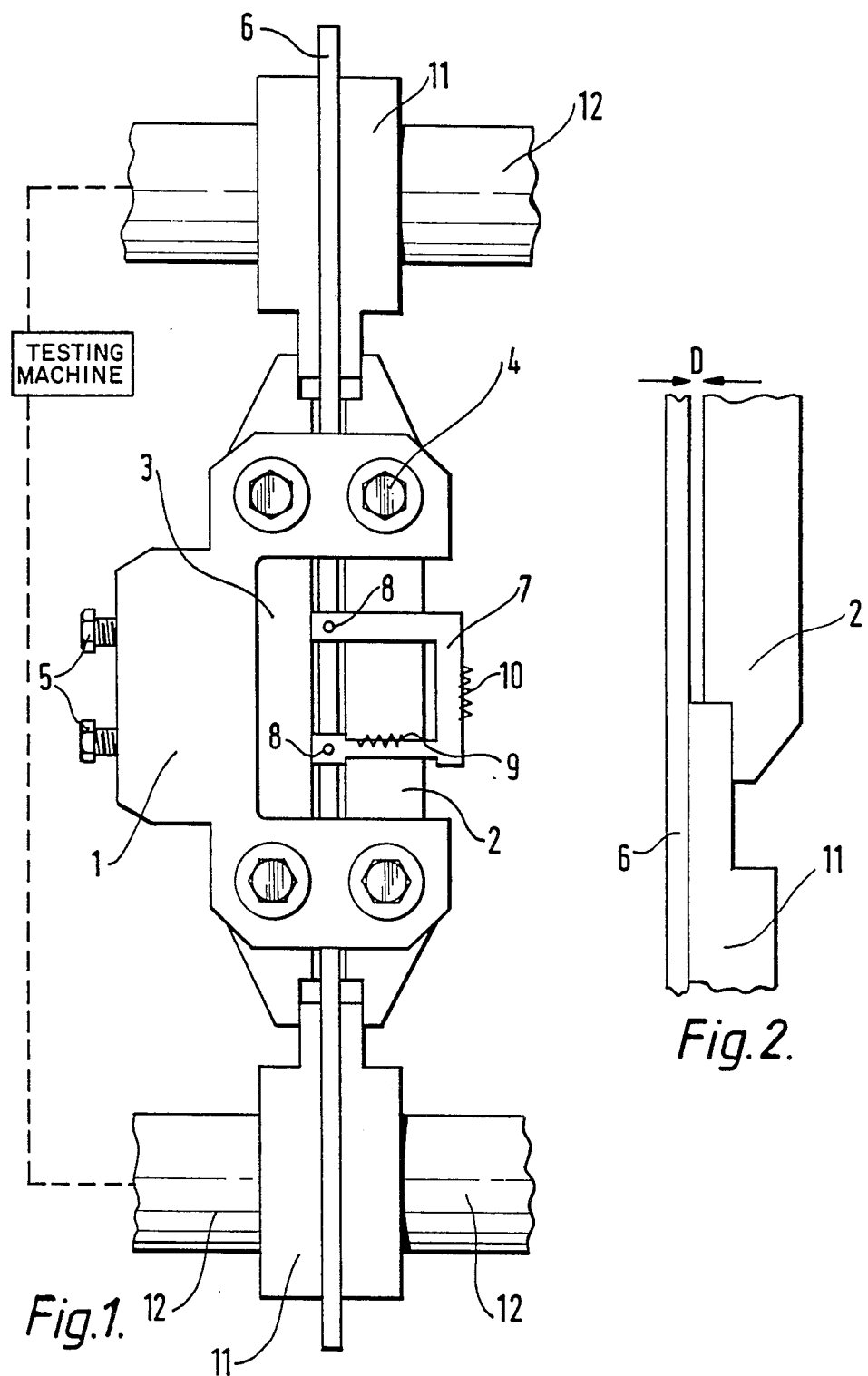
Figure 3:
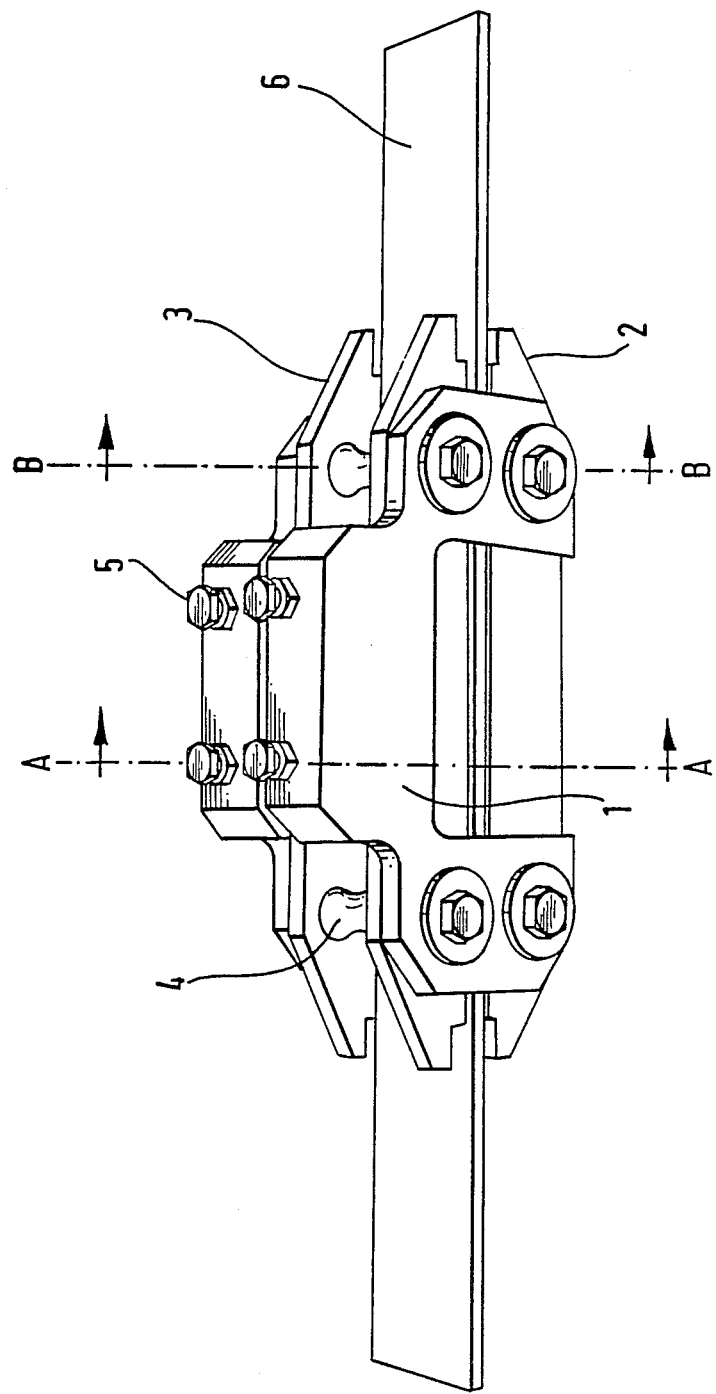
Figure 4:
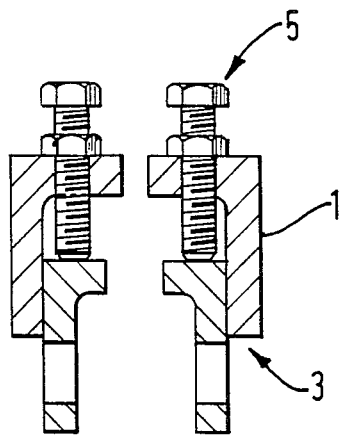
FIG. 4 is a fragmentary sectional view taken on line A—A of FIG. 3.
Figure 5:
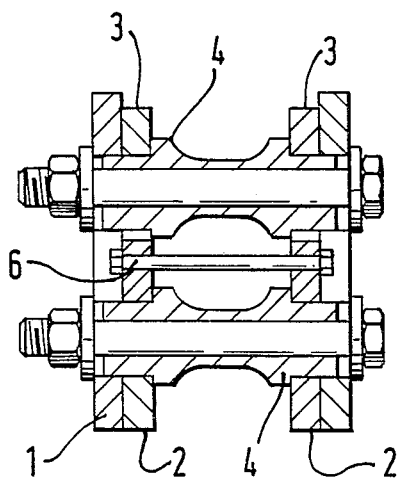
FIG. 5 is a sectional view taken on line B—B of FIG. 3.

Features common to two or more of the drawings have been given identical reference numbers. Referring to FIGS. 1 and 3 the stabiliser comprises two sets of brackets i.e. two external brackets 1 (forming a support body) and two pairs of internal brackets 2 and 3 (forming stabiliser members). The brackets are held apart at a fixed distance by spacers 4. One pair of brackets 2 is fixed to the external brackets 1, the other pair of brackets 3 is slideably mounted inside the brackets 1 and is adjustable by means of adjuster bolts 5. The pair of brackets 2 is fixed in place inside the brackets 1. The other pair of brackets 3 have elongated holes in their sides through which the spacers 4 pass; the elongated holes enable the inner bracket 3 to slide about the spacers and to be moved into engagement with grip inserts 11 to be described later under the action of adjuster bolts 5.

An extensometer bridge 7 is attached to the specimen by means of small grub screws 8. The bridge has extensometer resistors 9 and 10 bonded to it which measure deformation of the sample. The stabiliser engages with and is supported by the grip inserts 11 and the specimen 6 is gripped at both ends by grip inserts 11 and hydraulic pistons 12 of the compression test machine (not shown).

Initially the stabiliser is adjusted for a wide gap between brackets 2 and 3 so a specimen 6 can be readily inserted into the stabiliser. The sample and stabiliser are then placed into the compression test machine.

In operation the specimen of material 6, in this case a multi angular carbon fibre laminate, is placed between grip inserts 11 and secured between pistons 12 of the compression test machine. Pressure is applied to the grip inserts and ends of the specimen by the two pairs of opposed hydraulic pistons 12 so that they grip the specimen. A feature of the grip inserts is that they have spark eroded faces which enables them to be used in direct contact with the specimens under test in contrast to the known methods in which a protective plastic coating is required to be bonded to the ends of the specimen to prevent the specimen being nipped by the grip inserts and failing due to localised pressure from the grip inserts. The new spark eroded grip inserts eliminate the need for such a protective intermediate layer thus saving the time and expense of preparing specimens.

When the specimen is in place the stabiliser is adjusted so that the stepped edges of the internal brackets 2 and 3 make contact with the grip inserts 11. The adjuster bolts 5 are tightened so that the internal brackets 3 slide into firm contact with the grip inserts 11 and the whole stabiliser assembly is firmly supported but not clamped by the grip inserts so that the inserts may slide within the brackets 3 as the compression test proceeds. FIG. 2 is an enlarged detail of FIG. 1 and shows how one end of the bracket 2 makes contact with grip insert 11. It can be seen that although the grip insert 11 makes contact with the specimen, the bracket 2 remains a small predetermined distance D away from the specimen due to the relative proportions of the stepped edges of the bracket 2. The gap D is carefully selected to enable the specimen to buckle sufficiently to fail under compression but not enough to buckle and fail due to buckling. The gap D will remain constant no matter what thickness of specimen is used, for example, if a thicker specimen is used both the grip insert and bracket 2 will be displaced outwardly through the same distance and the relative gap between the two will remain constant. Thus the present stabiliser can be used for different thicknesses of sample without the need for different thickness of skin and without the drawbacks of the fixed gap stabilisers discussed earlier.

Another advantage of the stepped ends of the stabiliser is that the stabiliser interlocks with the grip inserts in such a way that lateral movement of the specimen and stabiliser is prevented, with respect to the grip inserts and this prevents failure of the specimen due to kinking. Conventional stabilisers usually have flat ends which do not engage with grip inserts, consequently the specimen and stabiliser are able to move during compression of the specimen. If the movement is large enough the specimen will kink and fail at one end, between the stabiliser and grip inserts.

In the arrangement shown the sides of the specimen protrude slightly beyond the side faces of the internal brackets 2 and 3 allowing the extensometer bridge 7 to be attached to the sides to the sample by small grub screws 8 which make point contact with the surface of the specimen. The extensometer bridge has three extensometers bonded to it to measure deformation of the specimen during compression. A pair of extensometers 9 measure deformation of the specimen down each side and another extensometer 10 measure changes across the width of the specimen (poissons ratio). The extensometer bridge enables the same set of strain gauges to be re-used on different samples thus reducing the wastage of strain gauges. Plain specimens can be quickly inserted into the present arrangement without the need for preparing the samples thus saving the time and cost of preparation.

We claim:

1. A stabiliser assembly for preventing premature failing of an elongate compression test specimen by buckling including:

a support body defining a passage region through which a test specimen is inserted, said support body comprising two generally parallel spaced U-shaped bracket members, the arms of one bracket member being rigidly interconnected by spacer means to the arms of the other bracket member with the bases of said members lying adjacent each other; and two generally parallel spaced pairs of stabiliser members carried between the arms of said bracket members, said stabiliser members of each pair being mounted in use one to each side of the inserted specimen, each stabiliser member having a longitudinal edge region which lies adjacent a length of the inserted specimen so that, if initial buckling of the inserted specimen occurs, the edge region is contacted by the inserted specimen and further buckling prevented, each stabiliser member being of a cross-sectional shape such that any buckling loads are resisted, at least one of said stabiliser members being adjustable with reference to the other so that test specimens of different thicknesses can be accommodated.

2. A stabiliser assembly according to claim 1 wherein the adjustable stabiliser members lie adjacent to the bases of the bracket members, and said bases are provided with adjustment means to effect their adjustment.

3. Apparatus for the compression testing of elongate test specimens including:

two pairs of grip block inserts, which pairs, in use, are located at or near the opposite ends of a test specimen and which are adapted to be located in a test machine wherein the blocks of each pair are urged together to grip the respective ends of the specimen between them, the grip blocks of each pair having parallel but oppositely facing surfaces extending towards the grip blocks of the other pair; and a stabiliser assembly according to any one of the preceding claims wherein at least a portion of the edge regions of the stabiliser members of each pair protrude beyond the support body, said protruding portions having parallel but oppositely facing surfaces extending towards the grip blocks but facing oppositely to said parallel surfaces on said grip blocks so that the surfaces upon the grip blocks and the surfaces upon the stabiliser members slidably engage one another, thereby providing support for both said stabiliser assembly and the test specimen during compression testing but not interfering therewith.

4. Apparatus according to claim 3 wherein the slidably engaging surfaces of the grip blocks and the stabiliser members are so arranged with reference to the edge regions of the stabiliser members that the stabiliser edge regions are maintained at a predetermined distance from the inserted test specimen before the latter is stressed irrespectively of the thickness of the inserted test specimen.

5. Apparatus according to claim 4 wherein those surfaces of the grip blocks which engage the inserted test specimen have a roughened, spark-eroded surface to improve grip.

6. Apparatus according to claim 3 wherein those surfaces of the grip blocks which engage the inserted test specimen have a roughened, spark-eroded surface to improve grip.

* * * * *